(12) United States Patent
Komata et al.

(10) Patent No.: US 7,754,927 B2
(45) Date of Patent: Jul. 13, 2010

(54) METHOD FOR PRODUCING 3,3,3-TRIFLUOROPROPIONYL CHLORIDE

(75) Inventors: Takeo Komata, Kawagoe (JP); Kenji Hosoi, Kasukabe (JP); Shinya Akiba, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 101 days.

(21) Appl. No.: 12/296,838

(22) PCT Filed: Mar. 29, 2007

(86) PCT No.: PCT/JP2007/056824
§ 371 (c)(1),
(2), (4) Date: Oct. 10, 2008

(87) PCT Pub. No.: WO2007/119585
PCT Pub. Date: Oct. 25, 2007

(65) Prior Publication Data
US 2010/0113834 A1    May 6, 2010

(30) Foreign Application Priority Data
Apr. 13, 2006  (JP) .............................. 2006-110451
Jul. 27, 2006  (JP) .............................. 2006-205206

(51) Int. Cl.
*C07C 51/58* (2006.01)
*C07C 51/04* (2006.01)

(52) U.S. Cl. ........................ 568/861; 568/863; 568/604

(58) Field of Classification Search ................ 568/861, 568/863, 604
See application file for complete search history.

(56) References Cited

U.S. PATENT DOCUMENTS

| 4,643,851 A | 2/1987 | Cheminal et al. |
| 5,659,078 A | 8/1997 | Ebmeyer et al. |
| 5,872,290 A | 2/1999 | Colson et al. |

FOREIGN PATENT DOCUMENTS

| JP | 59-98031 A | 6/1984 |
| JP | 8-104660 A | 4/1996 |
| JP | 11-302217 A | 11/1999 |

OTHER PUBLICATIONS

Albert L. Henne et al., "Fluorinated Amines", Journal of the American Chemical Society, 1995, pp. 1901-1902, vol. 77.
Ling Xiao et al., "Synthesis of some fluorinated acids, ketones and alcohols derived from 3,3,3-trifluoropropionic acid", Journal of Fluorine Chemistry, 1997, pp. 99-104, vol. 86.
Journal of the Chemical Society of Japan, 1956, pp. 591-594, vol. 77.
Journal of the Society of Japan, 1958, pp. 487-490, vol. 79.
Yakfa Cheung, "N-Bromosuccinimide: Direct Oxidation of Aldehydes to Acid Bromides", Tetrahedron Letters, 1979, pp. 3809-3810, vol. 20.
Istvan E. Marko et al., "Radical Mediated Oxidations in Organic Chemistry. 3. an Efficient and Versatile Transformation of Aldehydes into Amides." Tetrahedron Letters, 1990, pp. 7237-7240, vol. 31., No. 49.
H. T. Clarke et al., O-Chlorobenzoyl Chloride, Organic Synthesis, Coll., 1941, p. 155-156, vol. 1.
International Search Report including English translation dated Jun. 26, 2007 (Three (3) pages).
Albert L. Henne et al., "Fluorinated Amines", Journal of the American Chemical Society, 1955, pp. 1901-1902, vol. 77.

*Primary Examiner*—Sikarl A Witherspoon
(74) *Attorney, Agent, or Firm*—Crowell & Moring, LLP (57) ABSTRACT

There is provided a process for producing 3,3,3-trifluoropropionyl chloride, which is characterized in that 3,3,3-trifluoropropionaldehyde is chlorinated by a chlorinating agent selected from the group consisting of chlorine ($Cl_2$), sulfuryl chloride ($SO_2Cl_2$) and organic N-chloro compounds.

11 Claims, 2 Drawing Sheets

METHOD FOR PRODUCING 3,3,3-TRIFLUOROPROPIONYL CHLORIDE

TECHNICAL FIELD

The present invention relates to a process for producing 3,3,3-trifluoropropionyl chloride, which is useful as an intermediate of medicines and agricultural chemicals and as a production raw material or synthesis intermediate of functional materials such as fluorine-containing polymers.

BACKGROUND OF THE INVENTION 3,3,3-trifluoropropionyl chloride is an extremely important compound as an intermediate of medicines and agricultural chemicals and as a production raw material or synthesis intermediate of functional materials such as fluorine-containing polymers. Hitherto, the following production processes have been reported.

In general, as a process for producing a carboxylic chloride, there is known a process of making the corresponding carboxylic acid into a carboxylic chloride by a chlorinating agent, such as thionyl chloride, phosphorus oxychloride, and phosphorus pentachloride.

As a process for producing 3,3,3-trifluoropropionyl chloride, Non-patent Publication 1 discloses a process in which $CF_3(CH_2)_2Cl$ is turned into a Grignard compound, followed by oxidation to obtain $CF_3(CH_2)_2OH$, and this is oxidized by chromic acid into 3,3,3-trifluoropropionic acid, followed by chlorination by phosphorus pentachloride to obtain 3,3,3-trifluoropropionyl chloride.

Non-patent Publication 2 discloses a process for obtaining 3,3,3-trifluoropropionyl chloride by chlorinating 3,3,3-trifluoropropionic acid with phthaloyl chloride.

Furthermore, there are known processes of turning fluorine atom-free, aromatic aldehydes and hydrocarbonaceous aldehydes into carboxylic bromides by N-bromo compounds such as N-bromosuccinic imide (Non-patent Publications 3-6). In particular, it is known that a compound, such as an aromatic aldehyde, having no hydrogen at α-position of a carbonyl carbon (α-position herein refers to a carbon site adjacent to the carbonyl carbon) is chlorinated by chlorine to give the corresponding carboxylic chloride (Non-patent Publication 7).

Non-patent Publication 1: Journal of the American Chemical Society, Vo. 77, pp. 1901-1902, the year 1955

Non-patent Publication 2: Journal of Fluorine Chemistry, Vol. 86, pp. 99-104, the year 1997

Non-patent Publication 3: Journal of the Chemical Society of Japan, Vol. 77, pp. 591-594, the year 1956

Non-patent Publication 4: Journal of the Chemical Society of Japan, Vol. 79, pp. 487-490, the year 1958

Non-patent Publication 5: Tetrahedron Letters, Vol. 20, pp. 3809-3810, the year 1979

Non-patent Publication 6: Tetrahedron Letters, Vol. 31, pp. 7237-7240, the year 1990

Non-patent Publication 7: Organic Syntheses, Coll. Vol. 1, p. 155, the year 1941

SUMMARY OF THE INVENTION

Process for producing 3,3,3-trifluoropropionyl chloride is publicly known. However, a process of chlorinating 3,3,3-trifluoropropionic acid by phosphorus pentachloride or phthalic chloride, which is described in Non-patent Publication 1 and Non-patent Publication 2, has had some problems as a process for industrially producing 3,3,3-trifluoropropionic acid, which is used as the raw material. That is, as mentioned above, hitherto the process for producing 3,3,3-trifluoropropionic acid is a multistep process. Furthermore, with respect to Non-patent Publication 1, it has been necessary to use chromic acid, which is difficult in handling in large amount. Furthermore, the above-mentioned chlorinating agents are not necessarily easy in handling, and furthermore 3,3,3-trifluoropropionic acid itself is high in corrosiveness. Therefore, there has been some difficulty in the industrial production.

Thus, it has been a task to establish a 3,3,3-trifluoropropionyl chloride production process, which is low in price and suitable for industrial production.

In view of the above problems, the present inventors have conducted an eager study to find a process that is suitable for industrial production of 3,3,3-trifluoropropionyl chloride. As a result, we have found that 3,3,3-trifluoropropionyl chloride represented by formula [2]

[Chemical Formula 2]

[2]

is obtained by reacting 3,3,3-trifluoropropionaldehyde represented by formula [1]

[Chemical Formula 1]

[1]

with a chlorinating agent selected from the group consisting of chlorine ($Cl_2$), sulfuryl chloride ($SO_2Cl_2$) and organic N-chloro compounds (hereinafter, the step of reacting this chlorinating agent is also referred to as "the first step").

In this first step, hitherto, there has not been known a technique in which an aldehyde compound that has no fluorine atom and has hydrogen atoms at α-position carbon site is reacted with a chlorinating agent for chlorination to produce the corresponding carboxylic chloride. For example, even if propionaldehyde is reacted with chlorine or sulfuryl chloride, the corresponding propionyl chloride is not obtained at all, but there are obtained a product having a chlorinated α-position carbon site and many other products (see Referential Examples 1-5).

Furthermore, in 3,3,3-trifluoropropionaldehyde represented by formula [1], which is the raw material of the present invention, a trifluoromethyl group ($CF_3$ group) exists at α-position carbon atom. It was expected that, due to strong electron attractive property of this trifluoromethyl group, reactivity of hydrogen atoms bonded to α-position carbon atom would become more unstable in terms of energy as compared with that having no trifluoromethyl group, and a tendency to induce side reactions would also be strong in contrast with the substrates hitherto disclosed in Non-patent Publications 3-7, and therefore it would be extremely difficult to produce 3,3,3-trifluoropropionyl chloride represented by formula [2].

The inventors, however, have obtained findings that the target 3,3,3-trifluoropropionyl chloride represented by formula [2] can be produced as a result of reacting a reaction substrate having such fluorine atoms with a chlorinating agent.

Hitherto, examples of bromination of a hydrocarbonaceous aldehyde containing no fluorine atom and of chlorination of an aromatic aldehyde containing no fluorine atom have been known (Non-patent Publications 3-7), but hitherto there has not been known an example in which a hydrocarbonaceous aldehyde having fluorine atoms reacts efficiently with the above-mentioned chlorinating agent as in the present step.

Furthermore, the present inventors have found that the above reaction proceeds particularly advantageously under a particular condition. In the present step, it is possible to obtain 3,3,3-trifluoropropionyl chloride represented by formula [2], which is the target product, by chlorinating 3,3,3-trifluoropropionaldehyde represented by formula [1]. Although details are described hereinafter, together with the target product, side reactions have been induced in some cases, such as generation of the products other than that, that is, 3,3,3-trifluoropropionic acid represented by formula [3], compounds represented by formula [4] to formula [6], in which chlorine has been introduced to α-position carbon atom, and other impurities (see Scheme 1).

[Chemical Formula 3]

The present inventors, however, have obtained findings that generation of the compounds represented by formula [4] to formula [6] is suppressed, and there improves selectivity of 3,3,3-trifluoropropionyl chloride represented by formula [2], which is the target product, by using a combination of particular conditions relative to such reaction substrate, that is, a radical initiator, such as organic peroxide and azo-series radical initiator, and low polarity solvent (In the present specification, a solvent having a relative dielectric constant of 15.0 or less refers to the low polarity solvent. The low polarity solvent refers to a nonpolar solvent, too), together with the above-mentioned chlorinating agent.

Furthermore, the present inventors also have obtained surprising findings that it is possible to dramatically suppress the above-mentioned compounds represented by formula [4] to formula [6] and to obtain the target 3,3,3-trifluoropropionyl chloride with a higher selectivity by changing the order of the addition into the reaction system upon obtaining 3,3,3-trifluoropropionyl chloride represented by formula [2], while combining the radical initiator and the low polarity solvent together with the above-mentioned chlorinating agent (see Examples 6 and 16).

It is assumed herein that the chlorinating agent reacts with the radical initiator, and chlorine radical (Cl.), which is a reaction active species, tends to occur, by making a condition in which the chlorinating agent exists more in the reaction system (e.g., the reaction start time) in case that the radical initiator and the low polarity solvent have been combined, and thereby the target product is highly selectively obtained by the reaction of 3,3,3-trifluoropropionaldehyde represented by formula [1] with the chlorine radical.

Thus, it is possible in the present invention to produce 3,3,3-trifluoropropionyl chloride represented by formula [2] with high selectivity by using the above-mentioned chlorinating agent and by following a condition of suitably combining the radical initiator and the low polarity solvent and a condition of changing the order of addition into the reaction system in relation to 3,3,3-trifluoropropionaldehyde represented by formula [1] and the chlorinating agent. It is therefore a very superior process in industrial scale production.

Furthermore, the present inventors have also found that 3,3,3-trifluoropropionic acid represented by formula [3]

[Chemical Formula 4]

can be obtained by hydrolyzing 3,3,3-trifluoropropionyl chloride that is represented by formula [2] and is obtained by the first step (hereinafter, this hydrolyzing step is also referred to as the second step).

Also regarding the above-mentioned compounds represented by formula [3] to formula [6], which had been generated in some cases besides the target product in the first step, it has also become possible to easily remove the compounds other than 3,3,3-trifluoropropionic acid represented by formula [3], by a normal purification operation after termination of the second step.

That is, the present invention provides a process for producing 3,3,3-trifluoropropionyl chloride represented by formula [2], comprising chlorinating 3,3,3-trifluoropropionaldehyde represented by formula [1] by a chlorinating agent selected from the group consisting of chlorine ($Cl_2$), sulfuryl chloride ($SO_2Cl_2$) and organic N-chloro compounds. Furthermore, it also provides a process for producing 3,3,3-trifluoropropionic acid represented by formula [3], comprising hydrolyzing the obtained 3,3,3-trifluoropropionyl chloride represented by formula [2].

DETAILED DESCRIPTION

According to the present invention, it is possible to produce 3,3,3-trifluoropropionyl chloride, which is useful as an intermediate of medicines and agricultural chemicals and as a production raw material or synthesis intermediate of functional materials such as fluorine-containing polymers, with low price and simplicity and efficiently in industrial scale, from 3,3,3-trifluoropropionaldehyde. An effect that it can be produced with a higher selectivity is shown by using a suitable combination of a radical initiator and a low polarity solvent.

In the following, the present invention is further described in detail. The present invention is a process for producing 3,3,3-trifluoropropionyl chloride represented by formula [2], which is characterized in that 3,3,3-trifluoropropionaldehyde represented by formula [1] is chlorinated by a chlorinating agent selected from chlorine ($Cl_2$), sulfuryl chloride ($SO_2Cl_2$) and organic N-chloro compounds (this step of producing 3,3,3-trifluoropropionyl chloride represented by formula [2] is also referred to as the first step).

Then, it is summarized as Scheme 2 in the following, including a step (it may be referred to as the second step) for producing 3,3,3-trifluoropropionic acid represented by formula [3] by hydrolyzing the obtained 3,3,3-trifluoropropionyl chloride represented by formula [2].

[Chemical Formula 5]

Firstly, the first step of the present invention is explained. The first step is a step for obtaining 3,3,3-trifluoropropionyl chloride represented by formula [2] by chlorinating 3,3,3-trifluoropropionaldehyde represented by formula [1] with a chlorinating agent selected from chlorine ($Cl_2$), sulfuryl chloride ($SO_2Cl_2$), and organic N-chloro compounds.

It is possible to produce 3,3,3-trifluoropropionaldehyde represented by formula [1], which is the starting raw material of the present step, by a conventional, publicly known process.

As the chlorinating agent used in the present step, chlorine ($Cl_2$), sulfuryl chloride ($SO_2Cl_2$), or an organic N-chloro compound is used. Specific examples of the organic N-chloro compound are N-chlorosuccinic imide, trichloroisocyanuric acid, and dichlorodimethylhydantoin. Each of these is useful as a chlorinating agent. Of these, chlorine, sulfuryl chloride and trichloroisocyanuric acid are particularly preferably used.

The amount of the chlorinating agent used is normally 0.8 moles to 3 moles, preferably 0.9 moles to 2.5 moles, more preferably 1 mole to 2 moles, relative to 1 mole of 3,3,3-trifluoropropionaldehyde represented by formula [1].

Of the chlorinating agents, however, in the case of organic N-chloro compounds, it can be used in a range that is the same as that of the above, normally in terms of chlorine atoms, relative to 1 mole of 3,3,3-trifluoropropionaldehyde represented by formula [1].

In reaction temperature, it is conducted normally at around 0° C.-150° C., preferably 15° C.-100° C., more preferably 30° C.-70° C. If the reaction temperature is lower than 0° C., the reaction is slow. If it is a temperature higher than 150° C., the production of isomers, as by-products, which have a chlorine atom(s) substituted at a different site(s), increase, apart from 3,3,3-trifluoropropionaldehyde represented by formula [1]. This may lower selectivity. Therefore, it is not preferable.

Regarding the condition of the chlorinating agent used in the present invention under ordinary temperature and ordinary pressure, it may be gaseous condition or solid condition without particular limitation and can suitably be selected by a person skilled in the art. The method of chlorination is not particularly limited, and it can be conducted by a flow system or batch manner or half-batch manner.

Furthermore, reaction pressure is not particularly limited, and the reaction can be conducted under ordinary pressure (atmospheric pressure) or pressurization.

For example, in case that the chlorinating agent is a gas, it is possible to introduce the chlorinating agent under ordinary pressure (atmospheric pressure) in a manner to turn one side of the reactor into an open system, or to conduct the reaction by using a pressure-proof reaction vessel under pressurized condition by closing the vessel. It is, however, preferable to introduce the chlorinating agent under ordinary pressure (atmospheric pressure) in a manner to turn one side of the reactor into an open system, since the chlorination proceeds sufficiently even under a mild condition.

Furthermore, in case that the chlorinating agent is a gas, it is effective to suitably use a method by a common means for increasing contact efficiency, such as gas introducing rate adjustment, a stirring device, a gas blowing device, or a sparger (a porous sparging tube).

In the case of conducting the reaction under pressurization, it is normally 0.1-10 MPa (absolute pressure, and it is the same hereinafter in the present specification), preferably 0.1-5 MPa, more preferably 0.3-2 MPa.

The reactor used in the present step is not particularly limited in material, as long as it is pressure-proof upon conducting the reaction under ordinary pressure or pressurization. It is possible to use a reactor lined with tetrafluoroethylene resin, chlorotrifluoroethylene resin, vinylidene fluoride resin, PFA resin, glass or the like, or a glass container. Even in the case of a reactor having an inner wall of stainless steel, iron or the like, the reaction itself proceeds. However, metal may be corroded by the chlorinating agent. Therefore, it is preferable to use the above-mentioned reaction vessel.

On the other hand, although hydrogen chloride gas is generated with the progress of the reaction irrespective of the type of the chlorinating agent, it can be discharged from the reaction region and trapped by water, alkali aqueous solution or the like.

In the present step, it is possible to make a radical initiator coexistent for further improving selectivity of the chlorination reaction towards the carbonyl carbon. Specifically, it is possible to preferably use an organic peroxide, an azo-series radical initiator, or light.

The organic peroxide can be exemplified by benzoyl peroxide (abbreviation: "BPO"), ketone peroxide, peroxy ketal, hydroperoxide, dialkyl peroxide, diacyl peroxide, peroxy ester, and peroxy dicarbonate.

The azo-series radical initiator can be exemplified by 2,2'-azobis(2-methylpropionitrile) (azobisisobutyronitrile, abbreviation: "AIBN"), 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 2,2'-azobis(2-(2-imidazolin-2-yl)propane)dihydrochloride, 2,2'-azobis(2-(2-imidazolin-2-yl)propane)disulfate, and 2,2'-azobis(2-methylpropionamidine) dihydrochloride.

Furthermore, in the case of using light as the catalyst upon conducting the present chlorination reaction, the light source is at least one selected from the group consisting of high-pressure mercury lamp, low-pressure mercury lamp, halogen lamp, UV lamp, tungsten lamp, light-emitting diode, and the like. Of these, halogen lamp and UV lamp are preferable.

In the case of using a radical initiator, the amount of the radical initiator used is normally 0.01-20 mol %, preferably 0.1-10 mol %, more preferably 0.5-5 mol %, relative to 1 mol of 3,3,3-trifluoropropionaldehyde represented by formula [1]. Observing the condition of progress of the reaction, it is also possible to suitably add the radical initiator. If the amount of the radical initiator is less than 0.01 mol % relative to μmol of the raw material, the reaction tends to terminate halfway, and there is a danger to lower yield. Therefore, it is not preferable. If it exceeds 20 mol %, it is not preferable economically. According to need, it is also possible to add the radical initiator in the middle of the reaction.

The reaction in the present invention can be conducted with no solvent, but solvent can also be used. Specifically, it is preferable to use a solvent having a relative dielectric constant in a range of 15.0 or less, as the low polarity solvent, in order to further improve selectivity of the chlorination reaction towards the carbonyl carbon of 3,3,3-trifluoropropionaldehyde represented by formula [1]. Of the low polarity solvents, an organic solvent having a relative dielectric constant in a range of 1.0-12.0 is preferable, and it is particularly preferable to use an organic solvent having a relative dielectric constant in a range of 1.8-10.0.

As a low polarity solvent having a relative dielectric constant in a range of 15.0 or less, it is possible to cite benzene (2.27), toluene (2.38), ethylbenzene (2.40), mesitylene (2.27), 1,4-dioxane (2.21), o-xylene (2.57), m-xylene (2.37), p-xylene (2.27), pentyl ether (2.77), naphthalene (2.54), p-dichlorobenzene (2.41), m-dichlorobenzene (5.04), o-dichlorobenzene (9.93), 2,4-dichlorobenzotrifluoride (2.0-15.0), 2,5-dichlorobenzotrifluoride (2.0-15.0), 2,2-dimethylpropane (1.80), 2-methylbutane (1.83), n-pentane (1.84), 2,2-dimethylbutane (1.87), n-hexane (1.88), 2-methylpentane (1.88), 2,3-dimethylbutane (1.89), 3-methylpentane (1.90), 2,4-dimethylpentane (1.91), 2-methylhexane (1.92), n-heptane (1.92), 3-methylhexane (1.93), 2,3-dimethylpentane (1.94), 2,2,4-trimethylpentane (1.94), n-octane (1.95), 2,2,3-trimethylpentane (1.96), cyclopentane (1.97), n-nonane (1.97), n-decane (1.99), n-dodecane (2.00), methylcyclohexane (2.02), cyclohexane (2.02), dibutyl ether (3.08), carbon tetrachloride (2.24), methylene chloride (8.93), and the like (one in parenthesis refers to relative dielectric constant).

Of these, p-dichlorobenzene, m-dichlorobenzene, o-dichlorobenzene, 2,4-dichlorobenzotrifluoride, 2,5-dichlorobenzotrifluoride, and carbon tetrachloride are preferable. In particular, p-dichlorobenzene and 2,4-dichlorobenzotrifluoride are particularly preferably used, since they are remarkably high in stability as compounds, resulting in difficulty in chlorination, and since they can easily be removed from 3,3,3-trifluoropropionyl chloride represented by formula [2] in a post-treatment stage.

Although the present reaction proceeds even with a solvent having a relative dielectric constant exceeding 15.0 (referred to as "polar solvent" in the present specification), for example, aprotic polar solvent, such as acetonitrile (37.5), N,N-dimethylformamide (DMF) (36.7), dimethylsulfoxide (DMSO) (46.7), and hexamethylphosphoric triamide (HMPA) (30.0) (see Examples 7 and 8), it is possible to further improve selectivity by using the above-mentioned low polarity solvent (one in parenthesis refers to relative dielectric constant).

The amount of the solvent used is normally 40-1000 weight %, preferably 60-700 weight %, more preferably 80-400 weight %, relative to 3,3,3-trifluoropropionaldehyde represented by formula [1].

The solvent can be used singly or as a mixed solvent of at least two kinds. In the case of using the mixed solvent, even if a solvent having a relative dielectric constant exceeding 15.0 is contained as a part of the component, it can preferably be used if relative dielectric constant of the entirety of the mixed solvent has a relative dielectric constant that is 15.0 or less. However, it is the simplest to use a solvent singly that satisfies the above condition.

In the present step, it is possible to suppress generation of the compounds represented by formula [4] to formula [6] by using a combination of the above-mentioned radical initiator and the nonpolar solvent together with the chlorinating agent upon chlorinating 3,3,3-trifluoropropionaldehyde represented by formula [1].

For example, upon using chlorine or sulfuryl chloride as the chlorinating agent (see Examples 1-16), it is possible to obtain 3,3,3-trifluoropropionyl chloride represented by formula [2], which is the target product, even under the condition of:

(1) a case in which only chlorine or only sulfuryl chloride is reacted (a condition in which the radical initiator and the low polarity solvent are not made to be coexistent) (see Examples 1 and 10).

It is, however, possible to highly selectively obtain 3,3,3-trifluoropropionyl chloride represented by formula [2] in the case of conducting the reaction under the following conditions of (2) to (4), (2) a case in which the reaction is conducted under nonexistence of the radical initiator and under the existence of the low polarity solvent (see Examples 3 and 11);

(3) a case in which the reaction is conducted under existence of the radical initiator and under nonexistence of the low polarity solvent (see Examples 2 and 12); and (4) a case in which the reaction is conducted under existence of the radical initiator and the low polarity solvent (see Examples 4-6, 9, and 13-16).

On the other hand, in case that an organic N-chloro compound is reacted as the chlorinating agent, it is possible to obtain the target compound even by a solvent other than the low polarity solvent (Example 17). It is, however, possible to obtain 3,3,3-trifluoropropionyl chloride represented by formula [2], which is the target product, with a higher selectivity by using the low polarity solvent (see Example 18).

The reaction manner in the present step is not particularly limited. Upon obtaining 3,3,3-trifluoropropionyl chloride represented by formula [2] by chlorinating 3,3,3-trifluoropropionaldehyde represented by formula [1], which is the raw material, by a chlorinating agent selected from chlorine, sulfuryl chloride and an organic N-chloro compound, the order of adding the chlorinating agent and 3,3,3-trifluoropropional-dehyde represented by formula [1], which are used, into the reaction system is changed by the present inventors. With this, it is possible to dramatically suppress the products shown in the above Scheme 1 other than 3,3,3-trifluoropropionyl chloride represented by formula [2] and to further highly selectively obtain the target product.

Specifically, it is possible to obtain the target product even by previously placing 3,3,3-trifluoropropionaldehyde represented by [1] and then by sequentially or continuously feeding the chlorinating agent. Herein, however, it is possible to dramatically suppress the compounds represented by formula [4] to formula [6], in which chlorine has been introduced to the α-position carbon atom as shown in Scheme 1, by a condition in which the above chlorinating agent exists in the reaction system in excess of 3,3,3-trifluoropropionaldehyde represented by formula [1] in the reaction, particularly in the initial stage of the reaction, that is, by firstly introducing the chlorinating agent and then continuously or sequentially adding 3,3,3-trifluoropropionaldehyde represented by formula [1], or by continuously or sequentially adding 3,3,3-trifluoropropionaldehyde represented by formula [1] while firstly introducing the chlorinating agent into the reactor.

Furthermore, it is possible to dramatically suppress the compounds represented by formula [4] to formula [6] also by adding the chlorinating agent simultaneously at the time of start of the reaction with 3,3,3-trifluoropropionaldehyde represented by formula [1] in equal amount.

For example, it is one of particularly preferable embodiments in the present invention that, after placing 2,2'-azobis(2-methylpropionitrile), while introducing chlorine at first, 3,3,3-trifluoropropionaldehyde represented by formula [1] is added in the present Example 6, or that, after placing 2,2'-azobis(2-methylpropionitrile), 3,3,3-trifluoropropionaldehyde and sulfuryl chloride are added dropwise simultaneously in Examples 8 and Example 16.

The reaction time is not particularly limited. It is preferable to terminate the reaction process after checking the condition of progress of the reaction by gas chromatography or the like and confirming that it has become closer to the end point.

Treatment after the reaction is not particularly limited. Treatment of the reaction products after the reaction may be conducted based on a normal organic synthesis treatment method. It is possible to obtain 3,3,3-trifluoropropionyl chloride represented by formula [2] by subjecting the reaction liquid to a normal means such as distillation.

In the present step, 3,3,3-trifluoropropionic acid represented by formula [3], which is the target product of the after-mentioned second step, may be produced, besides 3,3,3-trifluoropropionyl chloride represented by formula [2], but it is not problematic to use that directly as the raw material of the after-mentioned second step.

Furthermore, in the present step, even after using a normal means such as distillation on the reaction liquid, 3,3,3-trifluoropropionic acid represented by formula [3] and the compounds represented by formula [4] to formula [6] may remain (see Example 6 and Examples 16-18). A mixture containing these may, however, be used as the starting raw material of the after-mentioned second step (see Examples 19-21).

Although details are described hereinafter, it is possible to obtain 3,3,3-trifluoropropionic acid represented by formula [3],

[Chemical Formula 6]

[3]

by hydrolyzing 3,3,3-trifluoropropionyl chloride represented by formula [2] obtained by the present invention.

Next, the second step is explained. The second step is a step in which 3,3,3-trifluoropropionyl chloride represented by formula [2] obtained by the first step is hydrolyzed to obtain 3,3,3-trifluoropropionic acid represented by formula [3]. Hydrolysis referred herein refers to a decomposition reaction caused by action of water.

Although the amount of water used in the present step is not particularly limited as long as it is in 1 mole or greater relative to 1 mole of 3,3,3-trifluoropropionyl chloride represented by formula [2], which is the substrate. It is preferably 1-1000 moles, more preferably 1-100 moles. It is possible to use more than that, but it is not preferable since yield per volume of the inside of the reactor decreases.

The reaction temperature is normally −30° C. to +150° C., preferably −10° C. to +120° C., more preferably 0° C. to +100° C. If the reaction temperature is lower than −30° C., the reaction is slow. A temperature higher than 150° C. is not preferable, since there vaporize 3,3,3-trifluoropropionyl chloride represented by formula [2], 3,3,3-trifluoropropionic acid represented by formula [3], which is gradually produced during the progress of the reaction and is the target product, water used for the hydrolysis, and the like.

In the present step, hydrolysis may be conducted under the presence of acid. For example, in the case of using acid, the acid used is not particularly limited as long as it is a Brønsted acid. It can be exemplified by inorganic acids such as hydrochloric acid, sulfuric acid, nitric acid, phosphoric acid, silicic acid, hydrobromic acid and boric acid, and organic acids such as formic acid, acetic acid, propionic acid, butyric acid, valeric acid, pivalic acid, oxalic acid, succinic acid, adipic acid, crotonic acid, methanesulfonic acid and trifluoromethanesulfonic acid. Its amount for use changes according to valence of the acid used. For example, in the case of a monovalent acid, the amount of the acid used is 1 mole or greater, preferably 1-5 moles, relative to 1 mole of 3,3,3-trifluoropropionyl chloride represented by formula [2]. In the case of a bivalent acid, the amount of the acid used is 0.5 moles or greater, preferably 0.5-2.5 moles, relative to 1 mole of 3,3,3-trifluoropropionyl chloride represented by formula [2]. Although concentration of the acid is not particularly limited, 10% to 90% is preferable. The amount of water used in the case of conducting hydrolysis under the presence of acid is not particularly limited, as long as it is 1 mole or greater relative to 1 mole of 3,3,3-trifluoropropionyl chloride represented by formula [2], which is the substrate. It is preferably 1-1000 moles, more preferably 1-100 moles. In case that water is contained in the above-mentioned acid, that water may be used.

In the present step, however, hydrolysis proceeds sufficiently even by using only water. With this, it is possible to obtain 3,3,3-trifluoropropionic acid represented by formula [3], which is the target product.

Treatment after the reaction is not particularly limited. It is possible to obtain 3,3,3-trifluoropropionic acid represented by formula [3] by bringing the reaction liquid into contact with organic solvent to extract the target product into the organic phase and then subjecting it to a normal means such as distillation.

In the present step, in the case of using one containing 3,3,3-trifluoropropionic acid represented by formula [3] and the compounds represented by formula [4] to formula [6], which have been produced in some cases in the prior first step besides 3,3,3-trifluoropropionyl chloride represented by formula [2] and obtained by the first step (see Examples 19-21), the compounds represented by formula [4] to formula [6] or partial hydrolysates of the compounds represented by formula [4] to formula [6] may be obtained besides 3,3,3-trifluoropropionic acid that is represented by formula [3] and is the target product. It is, however, possible to easily remove compounds other than 3,3,3-trifluoropropionic acid represented by formula [3] by a normal purification operation after termination of the present step, thereby obtaining the target product with high yield.

In the following, the present invention is described in detail by examples, but it is not limited to these embodiments. Herein, "%" of the compositional analytical value represents "areal %" of the composition obtained by directly measuring the reaction mixture by gas chromatography (unless particularly described, detector is FID).

Example 1

Production of 3,3,3-trifluoropropionyl Chloride; Chlorine

A 50 ml, three-necked, glass flask equipped with a magnetic stirrer, a flowmeter, a thermometer, a condenser tube and a chlorine eliminating equipment was charged with 100 g (0.892 mol) of 3,3,3-trifluoropropionaldehyde, followed by heating to 50° C. under stirring. To this, chlorine (2.18 mol) was introduced at around 50° C. at a flow rate of 200 ml/min for 4 hours. Then, the reaction liquid was found by gas chromatography measurement to be 41.3% of 3,3,3-trifluoropropionyl chloride, 0.1% of 3,3,3-trifluoropropionic acid, 39.0% of 3,3,3-trifluoro-2-chloropropionaldehyde, 5.4% of 3,3,3-trifluoro-2,2-dichloropropionaldehyde, 9.2% of 3,3,3-trifluoro-2-chloropropionyl chloride and 5.0% of other impurities.

Spectrum Data 3,3,3-trifluoropropionyl chloride;
$^1$H-NMR spectrum (400 MHz, CDCl$_3$) δ (ppm): 3.75 (2H, q, J=9.2 Hz)
$^{19}$F-NMR spectrum (400 MHz, CDCl$_3$) δ (ppm): −64.85 (3F, t, J=9.2 Hz)
Mass spectrum (Obsd m/z); 146 (M$^+$), 111 (CF$_3$CH$_2$CO), 83 (CF$_3$CH$_2$), 69 (CF$_3$) 3,3,3-trifluoro-2-chloropropionaldehyde;
$^1$H-NMR spectrum (400 MHz, CDCl$_3$) δ (ppm): 4.58 (1H, q, J=6.1 Hz), 9.49 (1H, s)
$^{19}$F-NMR spectrum (400 MHz, CDCl$_3$) δ (ppm): −70.45 (3F, d, J=6.1 Hz)
Mass spectrum (Obsd m/z); 146 (M$^+$), 117 (CF$_3$CHCl), 82 (CF$_3$CH), 69 (CF$_3$) 3,3,3-trifluoro-2,2-dichloropropionaldehyde;
$^1$H-NMR spectrum (400 MHz, CDCl$_3$) δ (ppm): 9.29 (1H, s)
$^{19}$F-NMR spectrum (400 MHz, CDCl$_3$) δ (ppm): −74.99 (3F, s)
Mass spectrum (Obsd m/z); 181 (M$^+$+1), 151 (CF$_3$CCl$_2$), 132 (CF$_2$CCl$_2$), 116 (CF$_3$CCl), 97 (CF$_2$CCD, 69 (CF$_3$) 3,3,3-trifluoro-2-chloropropionyl chloride;
$^1$H-NMR spectrum (400 MHz, CDCl$_3$) δ (ppm): 5.01 (1H, q, J=5.6 Hz)
$^{19}$F-NMR spectrum (400 MHz, CDCl$_3$) δ (ppm): −71.26 (3F, d, J=5.6 Hz)
Mass spectrum (Obsd m/z); 180 (M$^+$, 145 (CF$_3$CHClCO), 117 (CF$_3$CHCl), 82 (CF$_3$CH), 69(CF$_3$)

Example 2

Production of 3,3,3-Trifluoropropionyl Chloride; Chlorine and AIBN

A 50 ml, three-necked, glass flask equipped with a magnetic stirrer, a flowmeter, a thermometer, a condenser tube and a chlorine eliminating equipment was charged with 30.0 g (0.268 mol) of 3,3,3-trifluoropropionaldehyde and 0.870 g (0.0053 mol) of 2,2'-azobis(2-methypropionitrile), followed by heating to 50° C. under stirring. To this, chlorine (0.218 mol) was introduced at around 50° C. at a flow rate of 20 ml/min for 4 hours. Then, the reaction liquid was found by gas chromatography measurement to be 52.2% of 3,3,3-trifluoropropionyl chloride, 1.8% of 3,3,3-trifluoropropionic acid, 2.9% of 3,3,3-trifluoro-2-chloropropionaldehyde, 3.1% of 3,3,3-trifluoro-2,2-dichloropropionaldehyde, 34.0% of 3,3,3-trifluoro-2-chloropropionyl chloride and 6.0% of other impurities.

Example 3

Production of 3,3,3-trifluoropropionyl Chloride; Chlorine and 2,4-dichlorobenzotrifluoride)

A 50 ml, three-necked, glass flask equipped with a magnetic stirrer, a flowmeter, a thermometer, a condenser tube and a chlorine eliminating equipment was charged with 30.0 g (0.268 mol) of 3,3,3-trifluoropropionaldehyde and 30.0 g of 2,4-dichlorobenzotrifluoride, followed by heating to 50° C. under stirring. To this, chlorine (0.218 mol) was introduced at around 50° C. at a flow rate of 20 ml/min for 4 hours. Then, the reaction liquid was found by gas chromatography measurement to be 9.0% of 3,3,3-trifluoropropionaldehyde of the raw material, 51.2% of 3,3,3-trifluoropropionyl chloride, 0.8% of 3,3,3-trifluoropropionic acid, 23.4% of 3,3,3-trifluoro-2-chloropropionaldehyde, 3.6% of 3,3,3-trifluoro-2,2-dichloropropionaldehyde, 11.5% of 3,3,3-trifluoro-2-chloropropionyl chloride and 0.5% of other impurities.

Example 4

Production of 3,3,3-trifluoropropionyl Chloride; Chlorine, 2,4-dichlorobenzotrifluoride and AIBN A 50 ml, three-necked, glass flask equipped with a magnetic stirrer, a flowmeter, a thermometer, a condenser tube and a chlorine eliminating equipment was charged with 30.0 g (0.268 mol) of 3,3,3-trifluoropropionaldehyde, 30.0 g of 2,4-dichlorobenzotrifluoride and 0.870 g (0.0053 mol) of 2,2'-azobis(2-methylpropionitrile), followed by heating to 50° C. under stirring. To this, chlorine (0.163 mol) was introduced at around 50° C. at a flow rate of 20 ml/min for 3 hours. Then, the reaction liquid was found by gas chromatography measurement to be 65.7% of 3,3,3-trifluoropropionyl chloride, 1.6% of 3,3,3-trifluoropropionic acid, 3.0% of 3,3,3-trifluoro-2-chloropropionaldehyde, 2.0% of 3,3,3-trifluoro-2,2-dichloropropionaldehyde, 24.6% of 3,3,3-trifluoro-2-chloropropionyl chloride and 3.1% of other impurities, except 2,4-dichlorobenzotrifluoride of the solvent.

Example 5

Production of 3,3,3-trifluoropropionyl Chloride; Chlorine, 1,2-dichlorobenzene and AIBN A 50 ml, three-necked, glass flask equipped with a magnetic stirrer, a flowmeter, a thermometer, a condenser tube and a chlorine eliminating equipment was charged with 30.0 g (0.268 mol) of 3,3,3-trifluoropropionaldehyde, 30.0 g of 1,2-dichlorobenzene and 0.870 g (0.0053 mol) of 2,2'-azobis(2-methylpropionitrile), followed by heating to 50° C. under stirring. To this, chlorine (0.163 mol) was introduced at around 50° C. at a flow rate of 20 ml/min for 3 hours. Then, the reaction liquid was found by gas chromatography measurement to be 1.0% of 3,3,3-trifluoropropionaldehyde, 66.0% of 3,3,3-trifluoropropionyl chloride, 1.4% of 3,3,3-trifluoropropionic acid, 0.2% of 3,3,3-trifluoro-2-chloropropionaldehyde, 0.7% of 3,3,3-trifluoro-2,2-dichloropropionaldehyde, 26.2% of 3,3,3-trifluoro-2-chloropropionyl chloride, and 4.5% of other impurities, except 1,2-dichlorobenzene of the solvent.

Example 6

Figure 1:
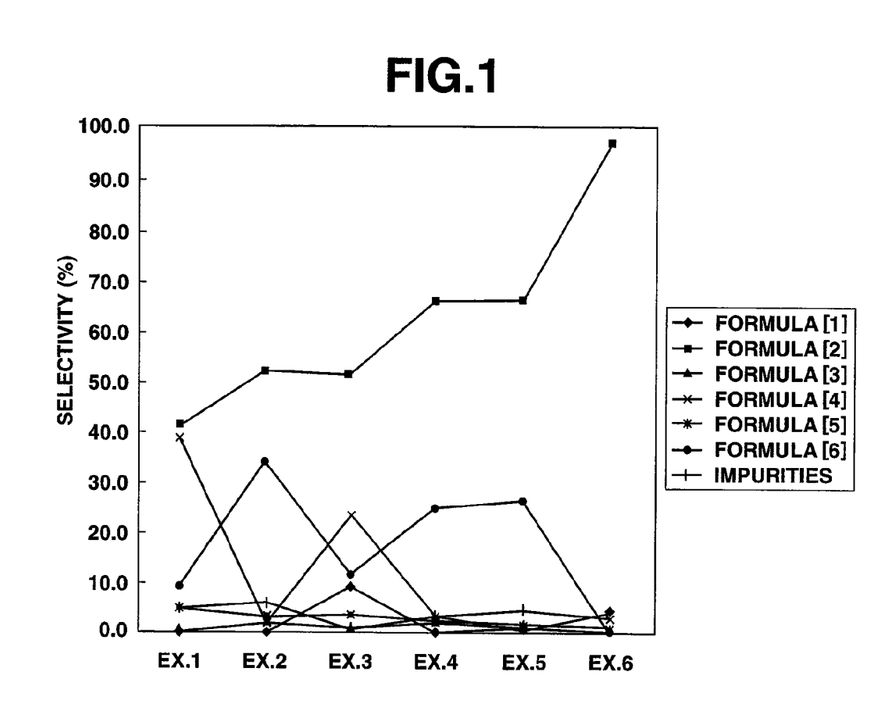
FIG. 1 shows a comparison of selectivities of the products obtained in Examples 1-6.

Production of 3,3,3-trifluoropropionyl Chloride; Chlorine, 2,4-dichlorobenzotrifluoride and AIBN A 50 ml, three-necked, glass flask equipped with a magnetic stirrer, a flowmeter, a thermometer, a condenser tube and a chlorine eliminating equipment was charged with 30.0 g of 2,4-dichlorobenzotrifluoride and 0.870 g (0.0053 mol) of 2,2'-azobis(2-methylpropionitrile), followed by heating to 50° C. under stirring. To this, while introducing chlorine (0.340 mol) at around 50° C. at a flow rate of 50 ml/min, 30.0 g (0.268 mol) of 3,3,3-trifluoropropionaldehyde was added with a syringe by spending 30 minutes. Then, heating and stirring were conducted at around 50° C. for 2 hours. The reaction liquid was found by gas chromatography measurement to be 96.2% of 3,3,3-trifluoropropionyl chloride, 0.7% of 3,3,3-trifluoropropionic acid, 0.3% of 3,3,3-trifluoro-2-chloropropionyl chloride, and 2.8% of other impurities, except 2,4-dichlorobenzotrifluoride of the solvent (selectivity of each compound in the reaction liquid obtained at this time is shown in FIG. 1).

Furthermore, for the purpose of separating 2,4-dicholorobenzotrifluoride used as the solvent and the product, the obtained reaction liquid was subjected to a simple distillation under ordinary pressure to collect a distillate of 40-70° C., thereby obtaining 25.2 g of the target 3,3,3-trifluoropropionyl chloride (purity: 97.4%; yield: 62.5%) (as others of this distillate, 3,3,3-trifluoro-2-chloropropionyl chloride (GC purity: 0.3%), 3,3,3-trifluoropropionic acid (GC purity: 0.1%), and other impurities (GC purity: 2.2%)).

Example 7

Production of 3,3,3-trifluoropropionyl Chloride; Sulfuryl Chloride, AIBN and Acetonitrile A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of acetonitrile, followed by heating to 50° C. under stirring. To this, 0.15 g (0.0009 mol) of 2,2'-azobis(2-methylpropionitrile) was added rapidly, followed by adding dropwise 9.0 g (0.0670 mol) of sulfuryl chloride by spending 5 minutes. Then, heating and stirring were conducted at around 50° C. for four hours. The reaction liquid was found by gas chromatography measurement to be 1.0% of 3,3,3-trifluoropropionaldehyde of the raw material, 16.9% of 3,3,3-trifluoropropionyl chloride, 14.9% of 3,3,3-trifluoro-2-chloropropionaldehyde, 41.1% of 3,3,3-trifluoro-2,2-dichloropropionaldehyde, and 26.1% of other impurities, except acetonitrile of the solvent.

Example 8

Production of 3,3,3-trifluoropropionyl Chloride; Sulfuryl Chloride, AIBN and Acetonitrile A 50 ml, four-necked, glass flask equipped with a magnetic stirrer, dropping funnels, a thermometer and a condenser tube (open system) was charged with 5.0 g of acetonitrile, followed by heating to 50° C. under stirring. To this, 0.15 g (0.0009 mol) of 2,2'-azobis(2-methylpropionitrile) was added rapidly, followed by simultaneously adding dropwise 5.0 g (0.0446 mol) of 3,3,3-trifluoropropionaldehyde and 9.0 g (0.0670 mol) of sulfuryl chloride from respective dropping funnels by spending 5 minutes. Then, heating and stirring were conducted at around 50° C. for four hours. The reaction liquid was found by gas chromatography measurement to be 34.0% of 3,3,3-trifluoropropionyl chloride, 0.5% of 3,3,3-trifluoropropionic acid, 17.5% of 3,3,3-trifluoro-2-chloropropionaldehyde, 6.7% of 3,3,3-trifluoro-2,2-dichloropropionaldehyde, and 41.3% of other impurities, except acetonitrile of the solvent.

Example 9

Production of 3,3,3-trifluoropropionyl Chloride; Sulfuryl Chloride, Toluene, and AIBN A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of toluene, followed by heating to 50° C. under stirring. To this, 0.15 g (0.0009 mol) of 2,2'-azobis(2-methylpropionitrile) was added rapidly, followed by adding dropwise 9.0 g (0.0670 mol) of sulfuryl chloride by spending 5 minutes. Then, heating and stirring were conducted at around 50° C. for two hours. The reaction liquid was found by gas chromatography measurement to be 26.0% of 3,3,3-trifluoropropionaldehyde of the raw material, 58.2% of 3,3,3-trifluoropropionyl chloride, 0.3% of 3,3,3-trifluoropropionic acid, 3.0% of 3,3,3-trifluoro-2-chloropropionaldehyde, and 12.5% of other impurities, except toluene of the solvent.

Example 10

Production of 3,3,3-trifluoropropionyl Chloride; Sulfuryl Chloride

A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde, followed by heating to 50° C. To this, 9.0 g (0.0670 mol) of sulfuryl chloride was added dropwise by spending 5 minutes. Then, heating and stirring were conducted at around 50° C. for four hours. The reaction liquid was found by gas chromatography measurement to be 18.0% of 3,3,3-trifluoropropionaldehyde of the raw material, 68.5% of 3,3,3-trifluoropropionyl chloride, 1.7% of 3,3,3-trifluoropropionic acid, 9.1% of 3,3,3-trifluoro-2-chloropropionaldehyde, 0.5% of 3,3,3-trifluoro-2,2-dichloropropionaldehyde, 1.2% of 3,3,3-trifluoro-2-chloropropionyl chloride, and 1.0% of other impurities.

Example 11

Production of 3,3,3-trifluoropropionyl Chloride; Sulfuryl Chloride and 2,4-dichlorobenzotrifluoride A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of 2,4-dichlorobenzotrifluoride, followed by heating to 50° C. under stirring. To this, 9.0 g (0.0670 mol) of sulfuryl chloride was added dropwise by spending 5 minutes. Then, heating and stirring were conducted at around 50° C. for four hours. The reaction liquid was found by gas chromatography measurement to be 17.7% of 3,3,3-trifluoropropionaldehyde of the raw material, 70.0% of 3,3,3-trifluoropropionyl chloride, 1.4% of 3,3,3-trifluoropropionic acid, 6.2% of 3,3,3-trifluoro-2-chloropropionaldehyde, 0.3% of 3,3,3-trifluoro-2,2-dichloropropionaldehyde, 0.7% of 3,3,3-trifluoro-2-chloropropionyl chloride, and 3.7% of other impurities, except 2,4-dichlorobenzotrifluoride of the solvent.

Example 12

Production of 3,3,3-trifluoropropionyl Chloride; Sulfuryl Chloride and BPO

A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde, followed by heating to 50° C. under stirring. To this, 0.29 g (0.0009 mol) of 75% benzoyl peroxide was added rapidly, followed by adding dropwise 9.0 g (0.0670 mol) of sulfuryl chloride by spending 5 minutes. Then, heating and stirring were conducted at around 50° C. for two hours. The reaction liquid was found by gas chromatography measurement to be 11.0% of 3,3,3-trifluoropropionaldehyde of the raw material, 72.5% of 3,3,3-trifluoropropionyl chloride, 0.4% of 3,3,3-trifluoropropionic acid, 5.3% of 3,3,3-trifluoro-2-chloropropionaldehyde, 0.4% of 3,3,3-trifluoro-2,2-dichloropropionaldehyde, 2.7% of 3,3,3-trifluoro-2-chloropropionyl chloride, and 7.7% of other impurities.

Example 13

Production of 3,3,3-trifluoropropionyl Chloride; Sulfuryl Chloride, BPO and 2,4-dichlorobenzotrifluoride A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of 2,4-dichlorobenzotrifluoride, followed by heating to 50° C. under stirring. To this, 0.29 g (0.0009 mol) of 75% benzoyl peroxide (a water-containing product) was added rapidly, followed by adding dropwise 9.0 g (0.0670 mol) of sulfuryl chloride by spending 5 minutes. Then, heating and stirring were conducted at around 50° C. for two hours. The reaction liquid was found by gas chromatography measurement to be 15.0% of 3,3,3-trifluoropropionaldehyde of the raw material, 76.4% of 3,3,3-trifluoropropionyl chloride, 0.3% of 3,3,3-trifluoropropionic acid, 2.6% of 3,3,3-trifluoro-2-chloropropionaldehyde, 0.4% of 3,3,3-trifluoro-2-chloropropionyl chloride, and 5.3% of other impurities, except 2,4-dichlorobenzotrifluoride of the solvent.

Example 14

Production of 3,3,3-trifluoropropionyl Chloride; Sulfuryl Chloride, BPO and 1,2-dichlorobenzene)

A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of 1,2-dichlorobenzene, followed by heating to 50° C. under stirring. To this, 0.29 g (0.0009 mol) of 75% benzoyl peroxide (a water-containing product) was added rapidly, followed by adding dropwise 9.0 g (0.0670 mol) of sulfuryl chloride by spending 5 minutes. Then, heating and stirring were conducted at around 50° C. for two hours. The reaction liquid was found by gas chromatography measurement to be 13.0% of 3,3,3-trifluoropropionaldehyde of the raw material, 79.3% of 3,3,3-trifluoropropionyl chloride, 3.1% of 3,3,3-trifluoro-2-chloropropionaldehyde, 0.7% of 3,3,3-trifluoro-2-chloropropionyl chloride, and 3.9% of other impurities, except 1,2-dichlorobenzene of the solvent.

Example 15

Production of 3,3,3-trifluoropropionyl Chloride; Sulfuryl Chloride, AIBN and 2,4-dichlorobenzotrifluoride A 50 ml, three-necked, glass flask equipped with a magnetic stirrer, a dropping funnel, a thermometer and a condenser tube (open system) was charged with 5.0 g (0.0446 mol) of 3,3,3-trifluoropropionaldehyde and 5.0 g of 2,4-dichlorobenzotrifluoride, followed by heating to 50° C. under stirring. To this, 0.15 g (0.0009 mol) of 2,2'-azobis(2-methylpropionitrile) was added rapidly, followed by adding dropwise 9.0 g (0.0670 mol) of sulfuryl chloride by spending 5 minutes. Then, heating and stirring were conducted at around 50° C. for two hours. The reaction liquid was found by gas chromatography measurement to be 6.0% of 3,3,3-trifluoropropionaldehyde of the raw material, 83.8% of 3,3,3-trifluoropropionyl chloride, 1.9% of 3,3,3-trifluoropropionic acid, 2.8% of 3,3,3-trifluoro-2-chloropropionaldehyde, 0.2% of 3,3,3-trifluoro-2,2-dichloropropionaldehyde, 1.2% of 3,3,3-trifluoro-2-chloropropionyl chloride, and 4.1% of other impurities, except 2,4-dichlorobenzotrifluoride of the solvent.

Example 16

Figure 2:
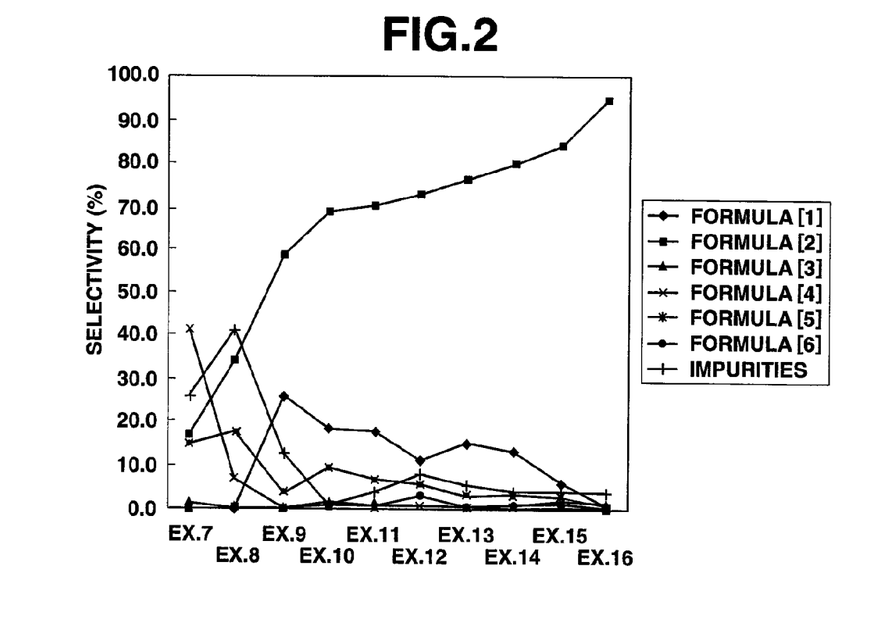
FIG. 2 shows a comparison of selectivities of the products obtained in Examples 7-16.
Figure 3:
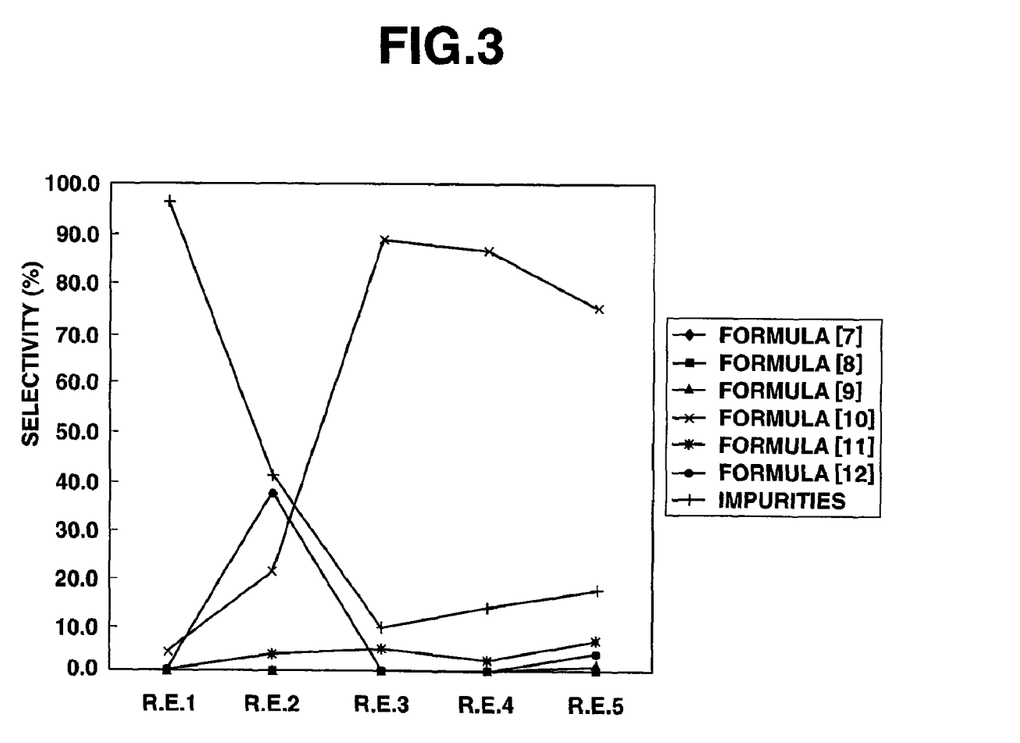
FIG. 3 shows a comparison of selectivities of the products obtained in Referential Examples 1-5.

Production of 3,3,3-trifluoropropionyl Chloride; Sulfuryl Chloride, AIBN and 2,4-dichlorobenzotrifluoride A 500 ml, four-necked, glass flask equipped with a magnetic stirrer, two dropping funnels, a thermometer and a condenser tube (open system) was charged with 100.0 g of 2,4- dichlorobenzotrifluoride, followed by heating to 50° C. under stirring. To this, 2.9 g (0.0177 mol) of 2,2'-azobis(2-methylpropionitrile) was added rapidly, followed by simultaneously adding dropwise 100.0 g (0.892 mol) of 3,3,3-trifluoropropionaldehyde and 132.4 g (0.981 mol) of sulfuryl chloride by spending one hour. After termination of the dropping, heating and stirring were conducted at 55-65° C. for one hour. The reaction liquid was found by gas chromatography measurement to be 0.4% of 3,3,3-trifluoropropionaldehyde of the raw material, 94.5% of 3,3,3-trifluoropropionyl chloride, 1.2% of 3,3,3-trifluoropropionic acid, 0.2% of 3,3,3-trifluoro-2-chloropropionaldehyde, 0.2% of 3,3,3-trifluoro-2-chloropropionyl chloride, and 3.5% of other impurities, except 2,4-dichlorobenzotrifluoride of the solvent (selectivity of each compound in the reaction liquid obtained this time is shown in FIG. 2).

For the purpose of separating 2,4-dichlorobenzotrifluoride used as the solvent and the product, the obtained reaction liquid was subjected to a simple distillation under ordinary pressure, thereby obtaining 145 g of a distillate of 40-70° C. The distillate was found by gas chromatography (detector: TCD) measurement to be 89.3% of the target 3,3,3-trifluoropropionyl chloride, 9.9% of sulfuryl chloride, and 0.8% of others.

Example 17

Production of 3,3,3-trifluoropropionyl Chloride; Trichloroisocyanuric Acid, and Acetonitrile A 50 ml, three-necked, glass flask equipped with a magnetic stirrer, a dropping funnel, a thermometer and a condenser tube (open system) was charged with 4.5 g (0.0193 mol) of trichloroisocyanuric acid and 10 g of acetonitrile, followed by heating to 50° C. under stirring. To this, 5.0 g (0.0446 mol) of 3,3,3-trifluoropropionaldehyde was added dropwise by spending 5 minutes. Then, heating and stirring were conducted at 50° C. for four hours. The reaction liquid was found by gas chromatography measurement to be 68.5% of 3,3,3-trifluoropropionyl chloride, 0.8% of 3,3,3-trifluoropropionic acid, 13.2% of 3,3,3-trifluoro-2-chloropropionaldehyde, 0.5% of 3,3,3-trifluoro-2-chloropropionyl chloride, and 17.0% of other impurities, except acetonitrile of the solvent.

Example 18

Production of 3,3,3-trifluoropropionyl Chloride; Trichloroisocyanuric Acid and 2,4-Dichlorobenzotrifluoride A 500 ml, three-necked, glass flask equipped with a mechanical stirrer, a dropping funnel, a thermometer and a condenser tube (open system) was charged with 89.9 g (0.387 mol) of trichloroisocyanuric acid and 200.0 g of 2,4-dichlorobenzotrifluoride, followed by heating to 50° C. under stirring. To this, 100 g (0.893 mol) of 3,3,3-trifluoropropionaldehyde was added dropwise by spending 15 minutes. Then, heating and stirring were conducted at 50° C. for two hours. The reaction liquid was found by gas chromatography measurement to be 1.0% of 3,3,3-trifluoropropionaldehyde of the raw material, 90.0% of 3,3,3-trifluoropropionyl chloride, 0.2% of 3,3,3-trifluoro-2-chloropropionaldehyde, and 8.8% of other impurities, except 2,4-dichlorobenzotrifluoride of the solvent.

After separating the precipitated solid by filtration, the filtrate was subjected to a simple distillation using a distillation column packed with an irregular packing made of glass to collect a distillate of 69° C. to 70° C., thereby obtaining 51.0 g (purity: 98.5%, yield: 51.0%) of the target 3,3,3-trifluoropropionyl chloride (as others of this distillate, 3,3,3-trifluoro-2-chloropropionaldehyde (GC purity: 0.4%) and other impurities (GC purity: 1.1%)).

Referential Example 1

Chlorine

Example 1 was repeated in operation and condition, except in that propionaldehyde was used in place of 3,3,3-trifluoropropionaldehyde. The reaction liquid was found by gas chromatography measurement to be 3.5% of 2-chloropropionaldehyde, 0.1% of 2,2-dichloropropionaldehyde, 0.1% of 2-chloropropionyl chloride, 0.3% of propionic acid, and 96.0% of others. The target propionyl chloride was not obtained at all.

Referential Example 2

Chlorine, 2,4-dichlorobenzotrifluoride, and AIBN

Example 6 was repeated in operation and condition, except in that propionaldehyde was used in place of 3,3,3-trifluoropropionaldehyde. The reaction liquid was found by gas chromatography measurement to be 20.3% of 2-chloropropionaldehyde, 3.2% of 2,2-dichloropropionaldehyde, 36.6% of 2-chloropropionyl chloride, 0.1% of propionic acid, and 39.8% of others. The target propionyl chloride was not obtained at all.

Referential Example 3

Sulfuryl Chloride

Example 10 was repeated in operation and condition, except in that propionaldehyde was used in place of 3,3,3-trifluoropropionaldehyde. The reaction liquid was found by gas chromatography measurement to be 87.6% of 2-chloropropionaldehyde, 4.1% of 2,2-dichloropropionaldehyde, and 8.3% of others. The propionyl chloride was not obtained at all.

Referential Example 4

Sulfuryl Chloride and 2,4-dichlorobenzotrifluoride

Example 11 was repeated in operation and condition, except in that propionaldehyde was used in place of 3,3,3-trifluoropropionaldehyde. The reaction liquid was found by gas chromatography measurement to be 85.4% of 2-chloropropionaldehyde, 1.6% of 2,2-dichloropropionaldehyde, and 13.0% of others. The propionyl chloride was not obtained at all.

Referential Example 5

Sulfuryl Chloride, 2,4-dichlorobenzotrifluoride and AIBN

Example 16 was repeated in operation and condition, except in that propionaldehyde was used in place of 3,3,3-trifluoropropionaldehyde. The reaction liquid was found by gas chromatography measurement to be 73.8% of 2-chloropropionaldehyde, 6.0% of 2,2-dichloropropionaldehyde, 3.2% of 2-chloropropionyl chloride, 0.5% of propionyl acid, and 16.5% of others. The propionyl chloride was not obtained at all.

Example 19

Production of 3,3,3-trifluoropropionic Acid

A 50 ml, three-necked, flask equipped with a magnetic stirrer and a condensing tube (open system) was charged with 25.2 g (173 mmol) of a mixture obtained by Example 6 and containing 3,3,3-trifluoropropionyl chloride (GC purity: 97.4%), 3,3,3-trifluoro-2-chloropropionic chloride (GC purity: 0.3%), 3,3,3-trifluoropropionic acid (GC purity: 0.1%), and other impurities (GC purity: 2.2%), followed by heating to 50° C. under stirring. Then, 3.4 g (190 mmol, 1.05 eq) of water was added to this. The reaction liquid obtained by heating and stirring for four hours was found by gas chromatography measurement to be 97.2% of 3,3,3-trifluoropropionic acid, 0.3% of 3,3,3-trifluoro-2-chloropropionic acid, and 2.5% of other impurities. After termination of the reaction, the obtained reaction liquid was directly subjected to an ordinary pressure distillation (boiling point: 136° C.), thereby obtaining the target 3,3,3-trifluoropropionic acid (yield: 18.7 g, yield: 84.5%, and purity: 99.9%).

Example 20

Production of 3,3,3-trifluoropropionic Acid

A 100 ml, three-necked, flask equipped with a magnetic stirrer and a condensing tube (open system) was charged with 100 g (685 mmol) of a mixture obtained by Example 16 and containing 3,3,3-trifluoropropionyl chloride (GC purity: 89.3%; detector: TCD), sulfuryl chloride (GC purity: 9.9%; detector: TCD), and other impurities (GC purity: 0.8%), followed by heating to 50° C. under stirring. Then, 12.9 g (719 mmol, 1.05 eq) of water was added to this. The reaction liquid obtained by heating and stirring for five hours was found by gas chromatography (detector: TCD) measurement to be 88.3% of 3,3,3-trifluoropropionic acid, 10.0% of sulfuryl chloride, and 1.7% of other impurities. After termination of the reaction, the obtained reaction liquid was directly subjected to an ordinary pressure distillation (boiling point: 136° C.), thereby obtaining the target 3,3,3-trifluoropropionic acid [yield: 61.4 g, yield: 70.5%, and purity: 99.9% (detector: TCD)].

Example 21

Production of 3,3,3-trifluoropropionic Acid)

A 50 ml, three-necked, flask equipped with a magnetic stirrer and a condensing tube (open system) was charged with 50.0 g (342 mmol) of a mixture obtained by Example 18 and containing 3,3,3-trifluoropropionyl chloride (GC purity: 98.5%), 3,3,3-trifluoro-2-chloropropionaldehyde (GC purity: 0.4%), and other impurities (GC purity: 1.1%), followed by heating to 50° C. under stirring. Then, 6.4 g (360 mmol, 1.05 eq) of water was added to this. The reaction liquid obtained by heating and stirring for five hours was found by gas chromatography measurement to be 98.2% of 3,3,3-trifluoropropionic acid, 0.4% of 3,3,3-trifluoro-2-chloropropionaldehyde, and 1.4% of other impurities. After termination of the reaction, the obtained reaction liquid was directly subjected to an ordinary pressure distillation (boiling point: 136° C.), thereby obtaining the target 3,3,3-trifluoropropionic acid (yield: 35.2 g, yield: 80.5%, and purity: 99.9% (detector: TCD).

The invention claimed is:

1. A process for producing 3,3,3-trifluoropropionyl chloride represented by formula [2],

[2]

comprising chlorinating 3,3,3-trifluoropropionaldehyde represented by formula [1]

[1]

by a chlorinating agent selected from the group consisting of chlorine (Cl$_2$), sulfuryl chloride (SO$_2$Cl$_2$) and organic N-chloro compounds.

2. A process according to claim 1, wherein the organic N-chloro compounds are N-chlorosuccinic imide, trichloroisocyanuric acid, and dichlorodimethylhydantoin.

3. A process according to claim 1, wherein, upon the chlorinating, a radical initiator is added.

4. A process according to claim 1, wherein, upon the chlorinating, a low polarity solvent having a relative dielectric constant of 15.0 or less is made to be coexistent.

5. A process for producing 3,3,3-trifluoropropionyl chloride represented by formula [2],

[2]

comprising chlorinating 3,3,3-trifluoropropionaldehyde represented by formula [1]

[1]

by chlorine (Cl$_2$) or sulfuryl chloride (SO$_2$Cl$_2$) in the presence of a radical initiator and a low polarity solvent having a relative dielectric constant of 15.0 or less.

6. A process according to claim 5, wherein the low polarity solvent having a relative dielectric constant of 15.0 or less is at least one solvent selected from the group consisting of dichlorobenzene, dichlorobenzotrifluoride, methylene chloride, and carbon tetrachloride.

7. A process according to claim 5, wherein the radical initiator is at least one selected from the group consisting of an organic peroxide, an azo-series radical initiator, halogen light, and UV light.

8. A process according to claim 7, wherein the organic peroxide is at least one selected from the group consisting of benzoyl peroxide, ketone peroxide, peroxy ketal, hydroperoxide, dialkyl peroxide, diacyl peroxide, peroxy ester, and peroxy dicarbonate.

9. A process according to claim 7, wherein the azo-series radical initiator is at least one selected from the group consisting of 2,2'-azobis(2-methylpropionitrile), 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 2,2'-azobis(2-(2-imidazolin-2-yl)propane)dihydrochloride, 2,2'-azobis(2-(2-imidazolin-2-yl)propane)disulfate, and 2,2'-azobis(2-methylpropionamidine)dihydrochloride.

10. A process for producing 3,3,3-trifluoropropionyl chloride represented by formula [2],

[2]

comprising chlorinating 3,3,3-trifluoropropionaldehyde represented by formula [1]

[1]

by chlorine ($Cl_2$) or sulfuryl chloride ($SO_2Cl_2$) in the presence of 2,2'-azobis(2-methylpropionitrile) and dichlorobenzotrifluoride.

11. A process for producing 3,3,3-trifluoropropionic acid represented by formula [3],

[3]

comprising:
(a) chlorinating 3,3,3-trifluoropropionaldehyde represented by formula [1]

[1]

by a chlorinating agent selected from the group consisting of chlorine ($Cl_2$), Sulfuryl chloride ($SO_2Cl_2$) and organic N-chloro compounds; thereby obtaining 3,3,3-trifluoropropionyl chloride represented by formula [2],

[2]

and
(b) hydrolyzing the 3,3,3-trifluoropropionic chloride.

* * * * *